United States Patent [19]

Lewy et al.

[11] Patent Number: 5,707,652

[45] Date of Patent: Jan. 13, 1998

[54] METHODS OF TREATING CIRCADIAN RHYTHM PHASE DISORDERS

[75] Inventors: Alfred J. Lewy; Robert L. Sack, both of Portland; Keith A. Parrott; James W. Ayres, both of Corvallis, all of Oreg.

[73] Assignee: State of Oregon, Portland, Oreg.

[21] Appl. No.: 480,558

[22] Filed: Jun. 7, 1995

Related U.S. Application Data

[63] Continuation of Ser. No. 97,443, Jul. 26, 1993, abandoned, which is a continuation-in-part of Ser. No. 842,723, Feb. 25, 1992, Pat. No. 5,242,941, which is a continuation of Ser. No. 621,866, Dec. 4, 1990.

[51] Int. Cl.$^6$ .................... A61K 9/52; A61K 9/54; A61K 9/22; A61K 9/26
[52] U.S. Cl. .................... 424/457; 424/458; 424/468; 424/469; 424/470; 424/471; 424/472; 514/415; 514/419
[58] Field of Search .................... 514/415, 419; 424/457, 458, 468, 469, 470, 471, 472

[56] References Cited

U.S. PATENT DOCUMENTS

| | | | |
|---|---|---|---|
| 2,853,420 | 9/1958 | Lowey | 167/82 |
| 3,538,214 | 11/1970 | Polli et al. | 424/19 |
| 3,835,221 | 9/1974 | Fulberth et al. | 424/20 |
| 4,083,949 | 4/1978 | Benedikt | 424/19 |
| 4,341,759 | 7/1982 | Bobentoft et al. | 424/21 |
| 4,505,890 | 3/1985 | Tain et al. | 424/21 |
| 4,572,833 | 2/1986 | Pedersen et al. | 424/20 |
| 4,600,723 | 7/1986 | Short et al. | 514/416 |
| 4,665,086 | 5/1987 | Short et al. | 514/416 |
| 4,882,137 | 11/1989 | Staples et al. | 424/423 |
| 4,945,103 | 7/1990 | Cohen . | |
| 5,169,642 | 12/1992 | Brinker et al. | 424/488 |
| 5,242,941 | 9/1993 | Lewy et al. | 514/416 |
| 5,449,588 | 9/1995 | Wurtman . | |

FOREIGN PATENT DOCUMENTS

| | | |
|---|---|---|
| 92303674.37 | 12/1992 | European Pat. Off. . |
| 00971 | 10/1988 | WIPO . |
| 01059 | 6/1989 | WIPO . |
| 01486 | 2/1992 | WIPO . |

OTHER PUBLICATIONS

Abstract, Lee et al., 1992 "Oral controlled release delivery system which mimics human circadian rhythm of melatonin", Amer. Assoc. Pharmac. Sci. Meeting, San Antonio, TX, Nov. 17, 1992, Abstract PDD 7162.

Abstract, Lee et al., 1992, "Evaluation of an oral controlled release delivery system which mimics human circadian rhythm of melatonin in human subjects", Western Pharmacy and Pharmacology Graduate Students' Meeting, Jul. 24, 1992.

Abstract, Lee et al., 1992, "Development of an oral sustained release delivery system for melatonin", Amer. Assoc. Pharmac. Sci. Meeting, Reno, NV, Mar., 1992.

Abstract, Lee et al., 1992, "Evaluation of an oral sustained release delivery system for melatonin in human subjects", Amer. Assoc. Pharmac. Sci. Meeting, Reno, NV, Mar., 1992.

Abstract, Lee et al., "Physicochemical properties of melatonin for dosage form design", Amer. Assoc. Pharmac. Sci. Meeting, Oct. 1991.

Abstract, Lee et al., 1991, "Transdermal delivery of melatonin in human subjects—pilot study", Amer. Assoc. Pharmac. Sci. Meeting, Reno, NV, Feb., 1991.

Lewy et al., 1992, "Melatonin shifts human circadian rhythms according to a phase–response curve", Chronobiol. Int'l 9: 380–392.

Nickelsen et al., 1991, "The effect of 6–, 9– and 11–hour time shifts on circadian rhythms: adaptation of sleep parameters and hormonal patterns following the intake of melatonin of placebo", Adv. Pineal Res. 5: 303–306.

Armstrong, 1991, "Treatment of sleep disorders by melatonin administration", Adv. in Pineal Res. 6: 263–274.

Samel et al., 1991, "Influence of melatonin treatment on human circadian rhythmicity before and after simulated 9–hr time shift", J. Biol. Rhythms 6: 235–248.

Van Coevorden et al., 1991, "Neuroendocrine rhythms and sleep in aging men", Am. J. Physiol. 260 (Endocrinol. Metab. 23):E651–E661.

Dahlitz et al., 1991, "Delayed sleep phase syndrome response to melatonin", The Lancet 337: 1121–1124.

Mallo et al, 1990, "Pharmacokinetics of melatonin in man after intravenous infusion and bolus injection", J. Clin. Pharmacol. 38: 297–301 (1990).

Armstrong, 1989, "Melatonin and circadian control in mammals", Experientia 45: 932–938.

Mallo et al., 1988, "Effects of a four–day nocturnal melatonin treatment on the 24 h plasma melatonin, cortisol and prolactin profiles in humans", Acta Endocrinol. 119: 474–480.

Arendt et al., 1987, "Some effects of jet–lag and their alleviation by melatonin", Ergonomics 30: 1379–1393.

Underwood, 1986, "Circadian Rhythms in Lizards: Phase Response Curve for Melatonin", J. Pineal Res. 3: 187–196.

Aldhous et al., 1985, "Plasma concentrations of melatonin in man following oral absorption of different preparations", Br. J. Clin. Pharmac. 19:517–521.

Arendt et al., 1985, "Some effects of melatonin and the control of its secretion in humans", CIBA Found. Symp. 117: 266–283.

Lane and Moss, 1985, "Pharmocokinetics of melatonin in man: First pass hepatic metabolism", J. Clin. Endocrinol. Metab. 61: 214–1216.

(List continued on next page.)

*Primary Examiner*—Shep K. Rose
*Attorney, Agent, or Firm*—McDonnell Boehnen Hulbert & Berghoff

[57] ABSTRACT

Methods for treating circadian rhythm disorders and sleep disorders are described. The method involves oral administration of a sustained release composition of melatonin to produce a normal melatonin pattern when the normal pattern has been disrupted or is missing.

21 Claims, 8 Drawing Sheets

OTHER PUBLICATIONS

Waldhauser et al., 1984, "Melatonin in human body fluids: Clinical significance", in *The Pineal Gland*, (R. Reiter, ed.), Raven Press: New York, p. 359.

Arendt et al., 1984, "The effects of chronic, small doses of melatonin given in the late afternoon on fatigue in man: A preliminary study", Neurosci. Lett. 45: 317–325.

Iguchi et al., 1982, "Melatonin serum levels and metabolic clearance rate in patients with liver cirrhosis", J. Clin. Endocrinol. Metab. 54: 1025–1027.

Gwinner, 1978, "The effects of pinealectomy on circadian locomotor activity rhythms in European starlings, *Sturnus vulgaris*", J. Comp. Physiol. 126: 123–129.

METHODS OF TREATING CIRCADIAN RHYTHM PHASE DISORDERS

This application is a continuation of application Ser. No. 08/097,443, filed Jul. 26, 1993, now abandoned which is a continuation-in-part of U.S. patent application Ser. No. 07/842,723, filed Feb. 25, 1992, now U.S. Pat. No. 5,242, 941, which is a continuation of U.S. patent application Ser. No. 07/621,866, filed Dec. 4, 1990.

BACKGROUND OF THE INVENTION

1. Field of the Invention

The field of the invention disclosed in this application relates to the regulation of circadian rhythms in humans, and to the synchronization of circadian rhythms with the external environment. Specifically, this invention describes a method to achieve a chronobiologic effect in humans. In particular, this invention relates to the reestablishment of synchrony between a human's endogenous biological circadian rhythm and the external environment (including the sleep-wake cycle) after its disruption in any of a number of ways.

In addition, this invention relates to methods and compositions to achieve normal melatonin patterns in humans having melatonin deficiency syndrome.

2. Background of the Related Art

The phenomenon of circadian rhythms in biology is well known, and circadian rhythms are exhibited by all eukaryotic plants and animals, including man. Biological rhythms are periodic fluctuations in biologic properties over time; these include circadian as well as seasonal variations. Circadian, or approximately 24-hour, rhythms include the production of biological molecules such as hormones, the regulation of body temperature, and behaviors such as wakefulness, sleep and periods of activity. In nature, circadian rhythms are closely tied to environmental cues that impose a 24-hour pattern on many of these fluctuations. An example of longer patterns that also involve the effect of hormones includes the menstrual cycle. Experimental inquiry has established that when environmental cues are absent, most apparent 24-hour circadian rhythms have a periodicity of approximately 25 hours. Circadian rhythms that are not regulated by environmental cues are said to be free-running. The regulation of circadian rhythms by signals from the environment is said to involve entrainment of the circadian rhythms. The environmental signals that effect entrainment have been termed zeitgebers, an example of which is the light-dark cycle.

It is thought in the art that the control of circadian rhythms in mammals is mediated by a portion of the brain called the superchiasmatic nuclei (SCN). One of the major circadian rhythms, that of wakefulness and sleep, is mediated by a feedback loop involving the retina, the SCN and the pineal gland. Melatonin, an indoleamine, N-acetyl-5-methoxytryptamine, is a neurohormone secreted primarily by the pineal gland in a circadian rhythm. This neurohormone is believed to be a physiological zeitgeber in some species.

The disruption of circadian rhythms in either timing or amplitude can reflect and possibly result in a number of pathophysiological states in humans. Disruption of normal circadian rhythms can occur when the timing of melatonin production, or the amplitude or duration of the melatonin pattern is abnormal. For example, the former is commonly associated with jet lag and the latter with aging.

As with all hormones, a disruption of a normal hormonal pattern cam result in a variety of physiological changes and in many apparently unrelated outcomes. These outcomes can be improved by modifying, restoring, or mimicking the normal hormonal pattern. Although the definitive human physiological function of melatonin remains unknown, it has been suggested to have a role in, for example, schizophrenia, sudden infant death or crib death syndrome, reproduction, thyroid function, migraine headache, sleep, seasonal affective disorder, shift worker syndrome, melatonin deficiency syndrome, pre-menstrual syndrome, appetite, contraception, mammalian breast and other carcinomas, immunostimulant and immunomodulatory effects, wool or hair production in animals, breeding, aging and depression, as well as jet lag.

U.S. Pat. Nos. 4,665,086 and 4,600,723 teach the use of melatonin to alleviate the symptoms of jet lag. These patents teach the use of 1–10 mg of melatonin, taken at destination bedtime, and again upon premature awakening in the middle of the night. A number of examples are disclosed in these patents, all involve travelers who take these doses of melatonin at destination bedtime and report the alleviation of the symptoms of jet lag.

It is known that melatonin in high pharmacological doses increase tiredness and the tendency to sleep in some people (see Arendt et al. Neurosci. Lett. 45: 317–325, 1984; Arendt et al. CIBA Found. Symp. 117:266–283, 1986).

Arendt et al., Ergonomics 30: 1379–1393 (1987), disclose the administration of melatonin to alleviate jet lag. Exogenous melatonin is administered orally from 4 to 6 hours prior to the human's normal bedtime. This schedule of melatonin was reported subjectively both to improve sleep quality and decrease sleep latency and to promote a more rapid reestablishment of the circadian rhythms of endogenous melatonin production.

Armstrong et al., Experientia 45: 932–938 (1989), disclose that in rats the effects of exogenous melatonin administration on the circadian rhythm of the sleep/wake cycle depend on the time of administration relative to the sleep/wake cycle, and that the effect was greatest when exogenous melatonin was administered a few hours before the effective start of the nocturnal activity cycle. However, these authors were unable to demonstrate phase-delay shifts; they also did not relate the timing of exogenous melatonin administration to the time of the endogenous melatonin onset.

Gwinner and Benzinger, J. Comp. Physiol. 126:123–129 (1978), teach that daily injections of melatonin can entrain the activity/rest cycle in birds.

Underwood, J. Pineal Res. 3:187–196 (1986), disclosed a phase response curve (PRC) for melatonin in the lizard *Sceloporus occidentalis;* they, as well, did not relate the timing of exogenous melatonin administration to the time of the endogenous melatonin onset.

Mallo et al., Acta Endocrinol. 119:474–480 (1988), teach that administration of 8 mg of melatonin to humans, one hour before bedtime over a course of four days, results in a slight phase advance three days after cessation of the melatonin treatment. However, not all rhythms advanced and there was no change in the melatonin rhythm the day after the last day of exogenous melatonin administration.

The prior art is replete with examples in medical therapy involving physiological replacement of natural occurring hormones to mimic hormonal patterns. Hormonal patterns are described by the timing (including onset time, offset time, and duration time) and amplitude of concentrations in the body or blood. Thus, hormonal treatment may include increasing the amplitude by administering exogenous hormone if the quantity produced internally is too small, increasing the duration if it is too short, or changing the onset or offset time.

Administration of hormones requires relatively uniform availability since normal ranges of hormone concentrations in the body are relatively narrow and reproducible within their circadian or normal rhythm patterns. Hormones are part of complicated feedback physiological activity loops, often resulting in a variety of outcomes depending on the stability of hormonal concentrations and phasic patterns. Products that result in large variations in availability of these agents are unacceptable in medical practice. Some estrogen hormonal products, for example, have been removed from the market because of unacceptable variations in blood concentrations and bioavailability.

Melatonin production by the pineal gland is essentially non-existent during the daytime. Sometime after dusk (often about 9 P.M.), melatonin levels increase 10- to 50-fold; the levels then decrease several hours later, either because of an endogenous mechanism or because of exposure to light in the morning, whichever happens first.

Strassman et al., J. Endocrin. Met., 66: 847–852 (1987) showed that melatonin plasma concentrations began rising steadily during normal sleep from below 10 picograms/ml (pg/ml) before 10 P.M. to about 40 pg/ml at 2 A.M., remained relatively sustained between about 40 and 55 pg/ml for about three hours until 5 A.M., and then declined back toward lower levels in the later morning. Van Coevorden et al., Am. J. Physiol., 260 (Endocrinol. Metab. 23): E651–E661 (1991), demonstrated that melatonin concentrations in normal young subjects ranged from about 58 to 92 pg/ml during the night with an average of 70 pg/ml while in the elderly the range was about 23–46 pg/ml with an average of about 37 pg/ml (data converted from reported concentrations originally presented in pM/l). This pattern, known as the daily rhythm of melatonin, is repeated every day with the onset time and offset (shut-off) time changing very little each day depending on the time of daylight and dusk.

Lane and Moss, J. Clin. Endrocrinol. Metab., 61: 1214–1216 (1985), disclosed that the increase in and maintenance of melatonin blood concentrations is due to its production by the pineal gland while its rapid clearance from the blood after production stops is due to rapid metabolism by the liver. Iguchi et al., J. Clin. Endrocrinol. Metab., 54: 1025–1027 (1982), reported the half-life of melatonin to be about 45 minutes following a 30-second injection in healthy Asian subjects. However, Mallo et al., J. Clin. Pharmacol. 38: 297–301 (1990), reported the half-life to be much shorter following bolus injections in European subjects, only about 28 minutes. The authors of the European study state that a difference between Asian and European people in their ability to metabolize melatonin cannot be ruled out as a possible explanation for these data.

Intravenous and oral administration of melatonin has usually involved pharmacological doses, so-called because they produce concentrations of melatonin that are up to several hundred times normal. After administration of a pharmacological dose, the drug is cleared from the body in a short time (not sustained so as to mimic a normal pattern).

Doses of melatonin in the range of 2 mg to 2,500 mg are considered pharmacological and not physiological. Melatonin is also remarkably non-toxic in large doses. Nevertheless, smaller doses are preferred over such pharmacological doses.

Although remarkably non-toxic, it is possible that immediate release pharmacological (large) doses of melatonin that fail to mimic normal patterns may produce down-regulation of melatonin receptors, i.e., such doses may produce a hormonal feedback loop effect. For example, it has been shown in hamsters that melatonin plasma levels in the physiologic range were effective while supraphysiologic doses (25 times greater than physiologic) were not effective. Also, Lane and Moss have suggested that high plasma concentrations of melatonin (expected to be five times normal) in liver disease patients produce a negative feedback effect to decrease melatonin production.

Moreover, it is generally considered good medical practice to administer the lowest effective dose of a drug, even a non-toxic drug, that will produce the desired effect. This is especially important if the plasma concentration patterns are shown to be highly variable such that a large dose of drug may peak very high in some subjects so that the peak concentration is outside normal physiologic concentrations. Further, economic factors weigh in favor of reduced doses. In addition to product cost, large doses may require extra doctor visits for dosage adjustment because of, for example, down-regulation of melatonin receptors.

Fifty milligram oral immediate release melatonin tablets, for example, produce average plasma melatonin concentrations of about 80,000 pg/ml, i.e., about 1600 times normal. This melatonin dosage form does not produce a sustained pattern of release: the concentration drops to about ¼ of the peak concentration in only about 3 hours. The bioavailability from oral doses containing at least 2.5 mg of melatonin is normally about 3% to 9%. However, bioavailability has been reported to be as high as 23% or 76% from an 80 mg dose. Similar decreases in bioavailability have been associated with reduced dosages of drugs such as melatonin that undergo extensive first pass metabolism. Furthermore, the fraction of the orally ingested dose absorbed was reported to vary by 25-fold among study subjects by F. Waldhauser et al., in The Pineal Gland, Russell Reiter, editor, Raven Press, New York, 1984, p. 359. They also noted that peak concentrations varied about 40-fold.

Such variations are not generally acceptable in medical practice and present serious problems in utilizing melatonin orally, even as an immediate release product. The problem is even more severe in hormone replacement or supplementation therapy where approximately normal hormonal patterns are desired. In such cases, 25-fold variation in bioavailability prevents development of a product to shift hormonal amplitude of a phasic curve into a normal range.

Administration of an oral sustained (slow) release formulation containing 2 mg of melatonin was shown by Aldhous et al. Br. J. Clin. Pharmac., 19: 517–521 (1985) to not be useful for mimicking normal melatonin patterns. The results were highly variable and plasma melatonin patterns were unlike normal melatonin patterns in both amplitude and duration. The maximum plasma concentrations, for example, were about 900 pg/ml in some cases while peaks occurred at either 2, 3, 4, 5, or 7 hours following the dose. In other cases the melatonin concentration was so low as to produce essentially no melatonin pattern over 4 or even 7 hours. In two of five cases the melatonin concentrations were about 9-fold normal and for some the concentrations were less than one-fifth of normal. Aldhous et al., further teach that the nutritional state of the individual greatly influences the melatonin pattern produced and that careful control of nutrition is necessary to control peak concentrations and the pattern of melatonin. Still, the best results from non-fasting subjects indicate that oral slow release melatonin cannot be used to mimic normal melatonin patterns.

Bioavailability from the 2 mg sustained release formulation is not reported. However, Aldous' results appear to indicate that the sustained release formulation provides no more than about 15% of the bioavailability expected from the 2 mg immediate release tablet (about 3% to 6% as taught by Lane and Moss). Thus, the prior art teaches that there is less than 1% bioavailability from oral sustained release melatonin.

In certain animals, including elderly rats and some elderly humans, night-time melatonin production is reduced from what is considered normal. This reduced melatonin production is termed Melatonin Deficiency Syndrome.

European Patent Application No. 0 518 468 A1 provides a method for correcting a melatonin deficiency syndrome comprising administering to a patient having the syndrome, over a predetermined time period including at least part of the nocturnal period, an amount of melatonin in controlled-release form, such that the melatonin is released according to a profile which, taking into account the existing profile, simulates the profile in plasma of a human being having a normal endogenous nighttime melatonin profile.

Entrainment and regulation of the melatonin circadian rhythm has thus been demonstrated in a number of animal species. The present inventors are the first to disclose a PRC for melatonin in a human. The ability to effect an actual change in phase of the circadian rhythm would be useful for the alleviation of a number of circadian rhythm related disorders, as will be further discussed in the embodiments below. This application discloses a method to advance or delay the onset of the production of endogenous melatonin, and hence actually affect the regulation of an endogenous circadian rhythm in man.

SUMMARY OF THE INVENTION

This invention relates to a method for achieving a chronobiologic effect in a human. This effect is achieved by regulation of a human's circadian rhythm. Specifically, the circadian phase-shifting effect is achieved by the administration of exogenous melatonin, which naturally occurs in the human only during the night. The timing of the nighttime onset of melatonin production in a particular individual will vary from person to person. The circadian rhythm of melatonin production in a human is entrained principally by the (bright) light-dark cycle and reflects a variety of other biological properties which vary with a circadian rhythm. The method of the invention entails the phase-shifting of the circadian rhythm by administration of exogenous melatonin. More specifically, the method of the invention involves the administration of a particular dosage of melatonin to the human. The particular dosage is lower than dosages taught by others, and is designed to achieve melatonin levels which are substantially equal to physiological levels in the human. Further, the method of the invention relates to the timing of the administration of the dosage of melatonin to the human. The timing of this dosage in the human is described to specifically phase-shift the circadian rhythm of endogenous melatonin production. The method described in the invention can be used to advance or delay the phase of the circadian rhythm of melatonin production in the human. In this way, the present invention is able to alleviate jet lag and other circadian rhythm disorders of both the phase-delay and the phase-advance types.

It has been discovered that the time of administration of exogenous melatonin relative to the time of endogenous melatonin onset is critical to the production of the appropriate phase-shifting effect. The time of administration of exogenous melatonin must be carefully set relative to the time of endogenous melatonin onset, preferably from more than 4 hours to about 8 hours before endogenous melatonin onset when a phase advance is desired, and about 9 hours to about 17 hours before endogenous melatonin onset when a phase-delay is desired. Since the endogenous melatonin onset typically occurs about 2 hours prior to when the normal sleep phase should begin, exogenous melatonin should be preferably administered from more than 6 hours to about 10 hours prior to the commencement of the patient's normal sleep phase when a phase-advance is desired, and about 11 hours to about 19 hours prior to the commencement of the patient's normal sleep phase when a phase-delay is desired. The preferred time of administration of exogenous melatonin for a particular individual human will be unique, depending on the individual's time of endogenous melatonin onset, which can vary markedly from individual to individual (between 7 PM to 11 PM for most individuals).

This invention also provides methods to mimic a normal melatonin pattern when the melatonin pattern is diminished because of a melatonin deficiency. This aspect of the invention contemplates administration of a sustained release melatonin formulation to a patient suffering from a deficiency of melatonin where the formulation comprises (a) a sugar-based core comprising less than about 1 mg of melatonin where the melatonin is about 0.05 to 2% by weight of the core; and (b) about 5 to 25% by weight of ethylcellulose coating comprising ethylcellulose and a plasticizer.

DETAILED DESCRIPTION OF THE PREFERRED EMBODIMENTS

By physiological levels or patterns is meant melatonin concentrations in the blood that mimic or are similar to normal concentrations in terms of timing, amplitude and duration.

By melatonin amplitude is meant a specific concentration of melatonin in the blood.

By melatonin duration is meant the length of time that a specific concentration of melatonin is present in the blood.

By onset time is meant the time [clock time or circadian time (defined below)] that a specific concentration of melatonin is reached in the blood. By circadian time is meant the time some internal pysiological event that occurs at some predictable time relative to the endogenous circadian pacemaker. For example, the onset of melatonin production occurs at circadian time (14 in most individuals).

By offset time is meant the time (clock time or circadian time) that a specific concentration of melatonin is no longer present in the blood.

By normal melatonin levels is meant ranges of melatonin such as those taught by Van Coevorden et al., and Strassman et al.

By a deficiency of melatonin is meant a melatonin concentration below the average normal concentration present in an individual at the time sleep is desired. Such melatonin deficiencies may be present when the individual is unable to produce a normal nighttime melatonin concentration. Low melatonin concentrations are common in the elderly and frequently have a low quality of sleep usually in combination with a decreased duration of sleep. In addition, a deficiency of melatonin at "bed time" typically exists in an individual suffering from jet lag.

When such low nighttime or bedtime concentrations of melatonin are present, the individual's melatonin or circadian rhythm is dispersed or shifted out of phase. Both of these circadian rhythm problems are addressable using the method of the present invention. Thus, the present invention encompasses the administration at the time sleep is desired of a sustained release melatonin composition that yields improved amounts of bioavailable melatonin and unexpectedly provides adequate melatonin levels in individuals suffering from a deficiency of melatonin.

Administration of sustained release melatonin or immediate release melatonin formulations corrects melatonin or circadian rhythms that are dispersed or shifted out of phase. When an individual is unable to produce a normal nighttime melatonin concentration, the administration of a sustained release formulation sets the individual's phase, i.e., the formulation provides a phase shift. Similarly, when a human is experiencing jet lag, administration of either sustained or immediate release melatonin at a specific, critical time effects a phase shift.

The amount of immediate release melatonin administered to the human patient should be sufficient to achieve the desired circadian phase-shifting effect. In a preferred embodiment of this invention, a dosage of about 0.25 mg to about 75 mg, preferably about 0.75 mg, and most preferably about 0.50 mg, of exogenous immediate release melatonin is used to effect the desired change in phase of the circadian rhythm of endogenous melatonin production. In a preferred embodiment, the total dose of immediate release melatonin is given in two or more smaller portions to the human patient over an interval of about two hours if the person is awake. One dose time is preferred if the person is asleep.

Pharmaceutical quality melatonin is commercially available. The dosage of melatonin may be administered orally, by injection, via a transdermal patch or by implantation of a reservoir designed to release a steady dosage of melatonin over time. In a preferred embodiment of this invention, melatonin is administered orally.

In a preferred embodiment of this invention, a phase advance in the circadian rhythm of endogenous melatonin production is effected by the administration of an amount of exogenous melatonin sufficient to achieve the phase advance from more than 6 hours to about 10 hours, preferably from about 7 to about 10 hours, most preferably about 8 hours, before the human's normal sleep phase should begin. This is typically from about 4 hours to about 8 hours, most preferably about 6 hours, before the patient's endogenous melatonin onset.

A phase delay in the circadian rhythm of endogenous melatonin production is effected by the administration of an amount of exogenous melatonin sufficient to achieve the phase delay from about 11 to about 19 hours, most preferably from about 12 to about 16 hours, prior to when the human's normal sleep phase should begin. This is typically from about 9 hours to about 17 hours, most preferably from about 10 to about 14 hours, before the patient's endogenous melatonin onset.

The amount of melatonin administered in the sustained release formulation to the human patient suffering from a melatonin deficiency should be sufficient to produce a normal nighttime melatonin amplitude, i.e., a plasma concentration approximating those in normal individuals at night. In a preferred embodiment of this invention, a dosage of about 0.025 mg to about 1 mg, more preferably from about 0.05 to 0.75 mg, and most preferably about 0.1 mg to about 0.4 mg, of sustained release melatonin is used to treat the patient and, thus, to mimic a normal melatonin pattern in the human during the time sleep is needed. Sustained release formulations containing higher amounts of melatonin will provide longer durations of release and, in addition, higher melatonin amplitudes in the patient.

It has unexpectedly been discovered that an oral sustained release melatonin formulation provides a sustained plasma concentration of melatonin over a period of at least three hours, and the dose required to achieve this concentration is substantially less than 1 mg. The sustained release melatonin formulation of the invention comprises (a) a core comprising 0.05 to 2% by weight of melatonin; and (b) about 5 to 25% by weight of ethylcellulose coating comprising ethylcellulose and a plasticizer. This formulation releases melatonin over time such that a normal nighttime amplitude of melatonin in the body is mimicked. The sustained release melantonin composition surprisingly provides at least about 5% bioavailable melatonin. In more preferred embodiments, the composition provides at least about 50% bioavailable melatonin, and more preferably at least about 10% bioavailable melatonin.

In preferred embodiments, the plasticizer is an alkyl sebacate or a trialkyl citrate, where each alkyl is the same or different and represents straight or branched chain alkyl groups having 1–6 carbon atoms. A particularly preferred plasticizer is a mixture of dibutyl sebacate and triethyl citrate at a ratio of about 1:1 by weight.

Those skilled in the art will recognize a variety of dosage forms that may be prepared to obtain a desired release pattern. Compositions containing the sustained release melatonin formulation may also contain one or more agents selected from the group consisting of sweetening agents, flavoring agents, coloring agents and preserving agents in order to provide pharmaceutically elegant and palatable preparations. Tablets may be prepared to contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby modify the sustained release of melatonin. For example, a time delay material such as glyceryl monosterate or glyceryl distearate may be employed.

Gelatin capsules may be prepared wherein the melatonin formulation is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. In a preferred aspect of the invention, particulate beads of the sustained release formulation were loaded into a gelatin capsule.

Administration of the sustained release formulation of the invention produces a melatonin amplitude that closely mimics the average nighttime pattern in terms of amplitude. This formulation produces less than a five-fold variation in the peak concentrations generated relative to normal; sustained patterns are over a period of about 3 to 10 hours where the average melatonin concentrations vary by less than five-fold. Preferred formulations according to the invention produce bioavailability of at least about 5%.

Mimicked (exogenously produced) normal melatonin patterns are defined as melatonin patterns in which the average melatonin concentration is between about one-fifth and five times normal and a sustained average concentration over a period of at least three hours where the plasma concentration does not fluctuate more than about five-fold. In preferred embodiments, the oral compositions produce a minimum concentration of at least one-third normal and no more than three times normal for a peak, with a sustained concentration over at least three hours where the concentrations fluctuate no more than three fold. Preferred oral doses of sustained release melatonin produce initial melatonin concentrations of from about 25 to 300 pg/ml, average melatonin concentrations of about 70 to 80 pg/ml over a three-hour period, and no more than three-fold variation in average concentrations over the three hours. Such products may be capsules or tablets or liquids so long as they provide a relatively sustained release over a time period of about 3 to 12 hours and usefully supplement or replace normal melatonin patterns. A useful dosage form can be produced using only controlled release melatonin without immediate release hormone.

Oral sustained release melatonin is useful to replace or supplement melatonin hormone in a truly physiologic pattern. This formulation can aid Alzheimer's patients and other elderly individuals.

The present invention may be used in, but is not limited to, the following situations to achieve chronobiologic effects, alleviate circadian rhythm disorders, and/or achieve normal concentrations of melatonin when initiation of sleep is desired via mimicking of normal melatonin patterns: astronauts in orbit around the earth, on missions in space to the Earth's moon or to the planets or out of the known solar system, or in training for such missions; submariners, or persons confined for research, exploration or industrial purposes below the seas; miners, explorers, spelunkers, researchers or those confined below the earth; psychiatric patients; insomniacs; the comatose, or those who need to be maintained in a state of unconsciousness for medical, psychiatric or other reasons; medical residents, nurses, firemen, policemen or all those whose duties require alertness and wakefulness at evening or nighttime hours, or those deprived of sleep for various periods because of their duties or responsibilities; the infantry, or other members of the armed forces whose duties require extreme levels of alertness and wakefulness, and who may be sleep deprived in the performance of duties; the blind or sight-impaired, or all those whose ability to distinguish differences in light and dark may be permanently or temporarily impaired; residents of the far North or Antarctica, or all those who live in a climate or climates that possess abnormal amounts of light or darkness; the aged, Alzheimer's patients, the sick, or all those who require dosages of medication at appropriate times in the circadian cycle; animal breeders, for use in controlling circadian time; schizophrenia, sudden infant death or crib death syndrome, reproduction, thyroid function, migraine headache, sleep, seasonal affective disorder, shift worker syndrome, melatonin deficiency syndrome, pre-menstrual syndrome, appetite affects, contraception, mammalian breast and other carcinomas, immunostimulant and immunomodulatory effects, wool or hair production in animals, breeding affects, aging effects, depression, as well as jet lag.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

1. Preparation of sustained release melatonin using 8–10 mesh sugar seeds and 20% ethylcellulose coating Melatonin was spray layered on 8–10 mesh non-peril sugar seeds to a concentration of 3.0 mg melatonin per gram of beads using polyvinylpyrrolidone (0.2%) and hydroxypropylcellulose (0.1%) with melatonin (0.6%) in 95% alcohol, in a spray coater. After drying, this product was then spray coated with ethylcellulose (Aquacoat®, FMC Corp.) containing 15% of solids weight of dibutyl sebacate and 15% of solids weight of triethyl citrate to a total calculated solids coating on the melatonin and sugar seeds of 20% by weight. Although some coating is lost during the spraying process, the final coat is at least about 10% by weight of the melatonin sustained release formulation and generally greater than 15% by weight, but less than 20%.

These beads demonstrate sustained release of melatonin in a controlled manner over about 8 hours in a United States Pharmacopia dissolution apparatus (basket method) with a time to 50% release of about 4 hours, stirring speed 50 rpm, in enzyme-free gastric fluid for the first 2 hours and then in enzyme-free intestinal fluid.

2. Preparation of sustained release melatonin using 18–20 mesh sugar seeds and 20% ethylcellulose coating Sustained release melatonin beads were prepared essentially as described in part 1 of this example except that 18–20 mesh non-peril sugar seeds were used.

These beads demonstrate sustained release of melatonin in a controlled manner in a United States Pharmacopia dissolution apparatus (basket method) with a time to 50% release of about 1 hour.

3. Preparation of sustained release melatonin using 8–10 mesh sugar seeds and 5% ethylcellulose coating Sustained release melatonin beads were prepared essentially as described in part 1 of this example except that the ethylcellulose coating was applied at about 5% by weight of the formulation.

These beads demonstrate sustained release of melatonin in a controlled manner in a United States Pharmacopia dissolution apparatus (basket method) with a time to 50% release of about 1 hour.

4. Preparation of sustained release melatonin using 8–10 mesh sugar seeds and 10% ethylcellulose coating Sustained release melatonin beads were prepared essentially as described in part 1 of this example except that the ethylcellulose coating was applied at about 10% by weight of the formulation.

These beads demonstrate sustained release of melatonin in a controlled manner in a United States Pharmacopia dissolution apparatus (basket method) with a time to 50% release of about 2 hours.

5. Preparation of melatonin composition containing sustained and immediate release melatonin Melatonin was spray layered on 8–10 mesh non-peril sugar seeds to a concentration of 3.0 mg melatonin per gram of beads using polyvinylpyrrolidone (0.2%) and hydroxypropylcellulose (0.1%) with melatonin (0.6%) in 95% alcohol, in a spray coater.

After drying, 0.04 mg or 0.02 mg of these immediate release melatonin beads were loaded into gelatin capsules with 0.36 mg or 0.18 mg of the sustained release melatonin beads prepared in part 1 of this example to result in a formulation containing 0.40 mg or 0.20 mg total melatonin.

A 0.80 mg melatonin formulation was prepared in a similar manner to contain 0.08 mg immediate release melatonin and 0.72 mg of sustained release melatonin.

6. Preparation of melatonin composition containing sustained release melatonin

Capsules were loaded to contain either 0.80 mg, 0.40 mg or 0.20 mg of the sustained release melatonin beads prepared in part 1 of this example were loaded into a gelatin capsule to result in formulations containing 0.80 mg, 0.40 mg or 0.20 mg total melatonin respectively.

EXAMPLE 2

Detection of Melatonin Levels in Human Plasma

Prior to collection of human blood, subjects are kept in dim light for about 5 hours (usually between 6 PM and 11 PM) except for the daytime studies. An intravenous line or heparin lock is inserted in a forearm vein and 5 ml of blood drawn at specified time periods such as every 30 minutes between 7 PM and 11 PM. The blood samples are centrifuged for 5 minutes at 1000 g and 4 degrees C., and the plasma aspirated into silanized glass or plastic tubes. Samples are assayed immediately or frozen for later analysis. To a 1 ml aliquot of such plasma was added 15–40 picograms of N-acetyl-5-methoxy($\alpha,\alpha,\beta,\beta$-D-4)tryptamine as a chromatographic control. An equal volume of normal saline is added and the mixture gently shaken with 10 volumes of petroleum ether. The organic phase is removed, and melatonin and the chromatographic control extracted from the aqueous phase with 10 volumes of chloroform. The aqueous phase is then discarded, and the chloroform evaporated to dryness.

The dried extract containing melatonin and the added chromatographic control is dissolved in 0.4 ml of anhydrous acetonitrile. The melatonin and the chromatographic control are then derivatized by the addition of 25 mcl of pentafluoropropionic acid anhydride and 0.5 ml of a solution of 5% trimethylamine in anhydrous benzene and reacted at 100 degrees C. for 10 minutes. The reaction products are washed sequentially with 1 ml water and 1 ml 5% ammonium hydroxide. The mixture is centrifuged briefly at 13,000 g and the organic phase withdrawn and evaporated to dryness under nitrogen. The dried extract is partitioned between 0.5 ml acetonitrile and 1 ml hexane by vigorous mixing followed by centrifugation. The hexane layer is removed and the acetonitrile evaporated to dryness under nitrogen. This partitioning step is performed two times for each sample. The dried extract is re-partitioned for storage. The derivatives are stable and can be stored at −20 degrees C. for several weeks.

The amount of melatonin present in each sample is determined by analysis using a gas chromatograph-mass spectrometer (GC-MS). Before injection onto the GC column, the dried derivatives are dissolved in 15 mcl of ethyl acetate. Approximately half this volume was applied to a 30×25 micron fused silica capillary column [0.15 micron film thickness with a 1 m retention gap (DB-225, J&W Scientific, Folsom, Calif.)]. The oven is programmed from 60 degrees C. to 240 degrees C. (at 25.5 degrees C./min) with helium as carrier gas (10 psi head pressure) and methane used as make-up gas (ionizer, 0.6 torr). Derivatized melatonin and chromatographic standard control are found to elute from the column after 10–14 minutes. Mass spectrographic analysis of the column eluate is then performed. Mass spectra are recorded using a Finnigan 4000-GC-CI analyzer and INCOS data system. A Finnigan PPIMCI electron multiplier with 3 kV conversion was used, signal referenced to ground. The relative signals of melatonin and the added chromatographic control are detected as m/e (mass/charge) ratios of 320 and 323, respectively. The amount of melatonin present in any unknown sample can be determined by comparisons of the ratio of the intensities of these signals to a standard curve, prepared as described using known amounts of melatonin and the chromatographic control.

EXAMPLE 3

1. Phase advance in blind subject using immediate release melatonin

Without light perception, blind people often have circadian rhythms that free run with a period greater than 24 hours. We have been successful in phase shifting a free-running circadian rhythm in at least one blind subject by administering capsules of 0.5 mg immediate release doses of melatonin orally.

Figure 1:
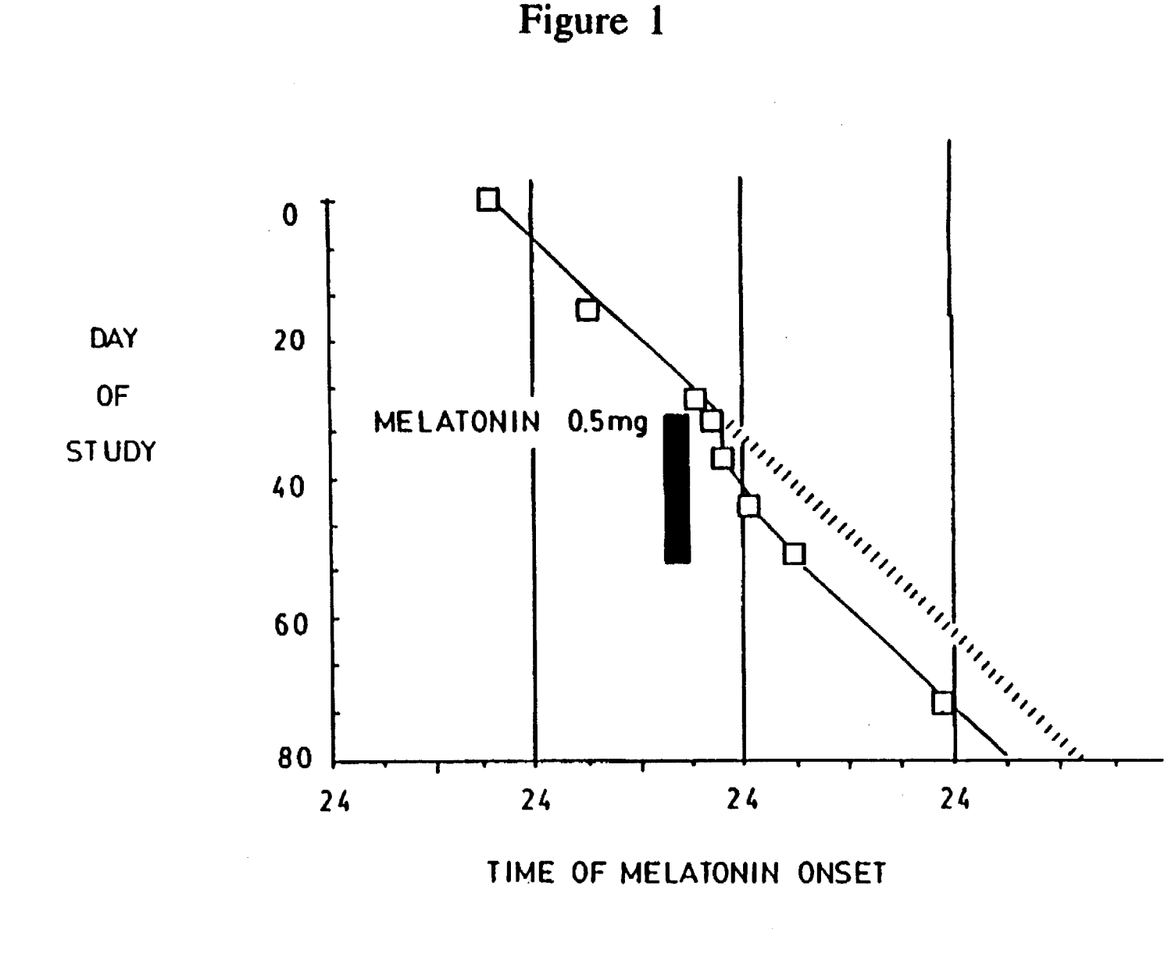
FIG. 1 discloses the experimental results of part 1 of Example 3, i.e., the effect of immediate release melatonin administration on endogenous melatonin onset.

A blind subject whose circadian rhythms were free-running was placed on a three-week regimen to phase shift his circadian rhythms using administration of exogenous melatonin. The subject was given 0.25 mg of melatonin orally at 1900 and 2100 hours (clock time) every day for three weeks. The effect of exogenous immediate release melatonin administration on the time of endogenous melatonin onset is shown in FIG. 1. The cumulative phase advance seen in this subject is equivalent to the phase advance obtained when a much higher dose (5 mg) was used. These results confirm that exogenous melatonin administration can effect a phase advance in a human.

Figure 8:
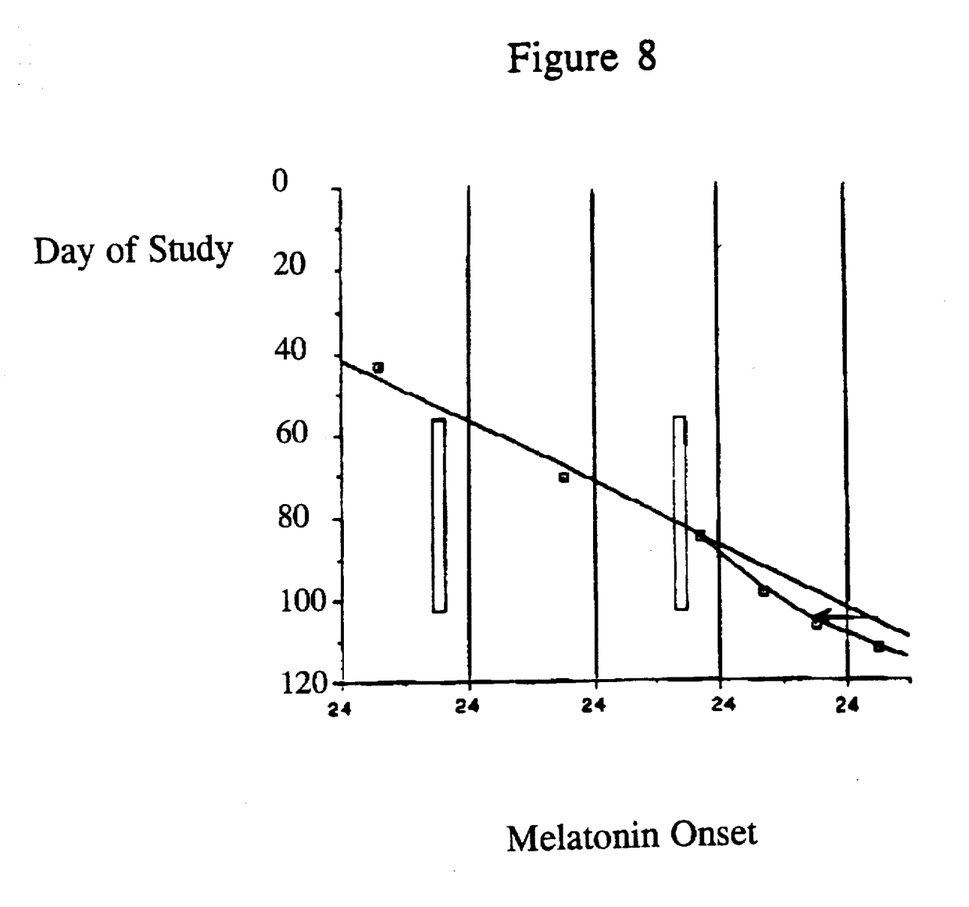
FIG. 8 is a graph of melatonin onset versus day of study for a patient administered 0.4 mg sustained release melatonin at 9 PM.

2. Phase advance in blind subject using immediate and sustained release melatonin Administration of 0.4 mg melatonin (0.04 mg immediate release and 0.36 mg sustained release) in a composition prepared as described above in part 5 of Example 1 to a blind patient who was also taking atenolol (100 mg) at 5 AM resulted in a circadian rhythm phase shift. The results shown in FIG. 8 demonstrate that a low dose of melatonin formulated to be partially immediate release and partially sustained release composition effects a phase advance in a human.

EXAMPLE 4

Mimicking of Normal Melatonin Patterns With Orally Administered Melatonin

Melatonin formulations as prepared in part 5 of Example 1 were administered during the daytime so the resulting melatonin patterns would not be confounded by normal (endogenous) melatonin production, since melatonin is only produced at night and daytime concentrations are always less than about 10 pg/ml. These capsules were administered at 9 AM either to six young (age 22 to 37) or six elderly (age 75 to 96) healthy fasting subjects, periodic blood samples were collected, and the samples were assayed using a specific binding radioimmunoassay (RIA) for melatonin as taught by Zimmerman et al., Fertil. Steril. 54: 612–618 (1990). Average melatonin concentrations and standard deviations were determined; the results from 0.8 mg, 0.4 mg and 0.2 mg melatonin formulations are shown in FIG. 2.

The results demonstrate that administration of an oral sustained release melatonin composition to human subjects mimics normal melatonin patterns. Circadian-phase shifting of endogenous melatonin can then occur during or following the periods when the melatonin levels are substantially equal to physiological patterns of melatonin. The example further shows that an oral controlled release composition with a low physiological dose can be administered orally to humans to replace or supplement therapy of this hormone.

Figure 2:
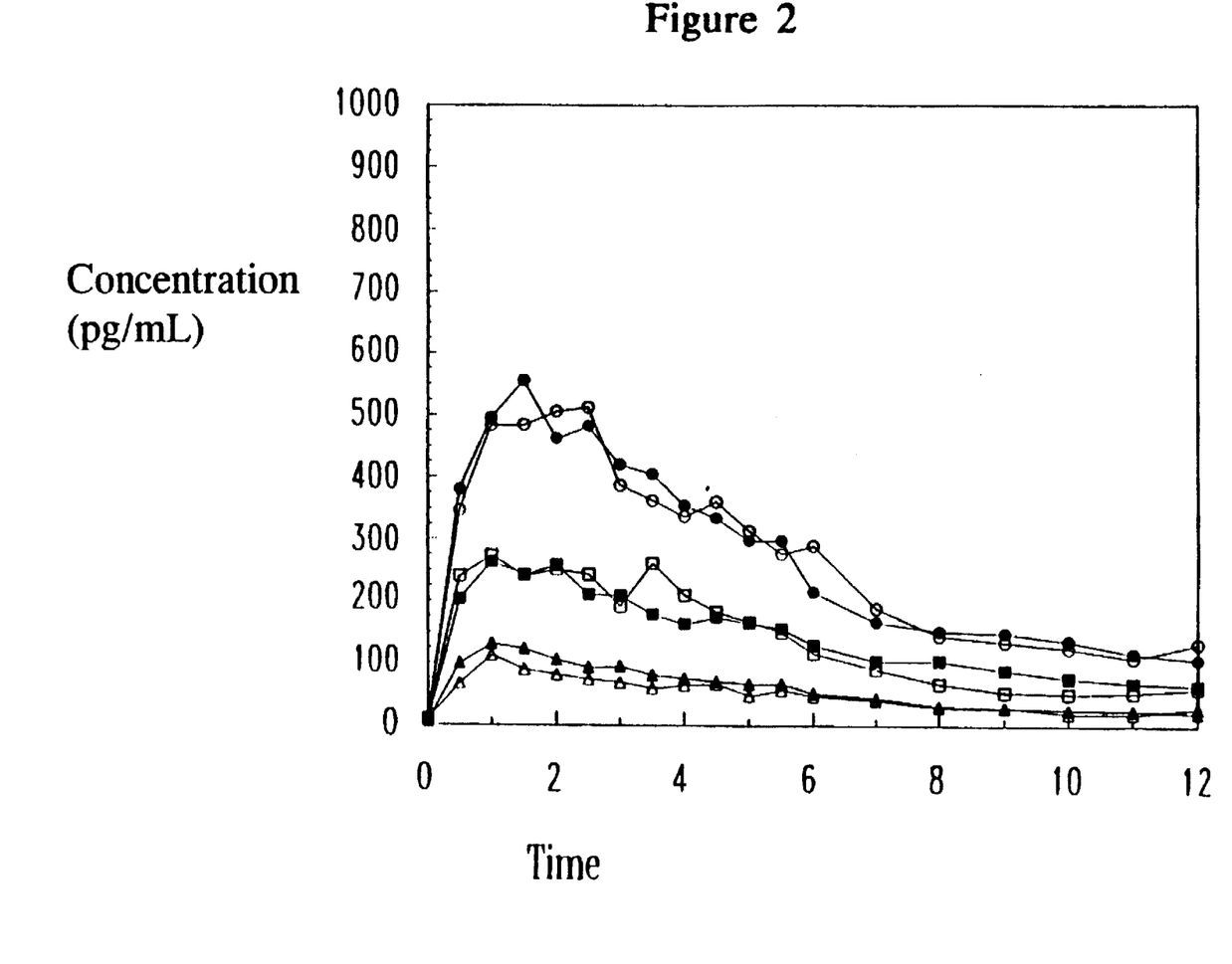
FIG. 2 is a graph of time in hours post-administration of a formulation comprising sustained and immediate release melatonin versus plasma melatonin concentrations for 0.8 mg (circles), 0.4 mg (squares), and 0.2 mg (triangles) in elderly (filled symbols) and young (open symbols) individuals.

FIG. 2 indicate that a 0.8 mg dose of melatonin combining 0.08 mg immediate release and 0.72 mg sustained release melatonin produced plasma concentrations above about 100 mg/ml for at leaset 12 hours in both elderly and young individuals.

FIG. 2 shows that a 0.4 mg dose of melatonin formulated as only 0.04 mg immediate release and 0.36 mg sustained release produced plasma melatonin concentrations above 100 pg/ml for about 6 hours in the young subjects and for about 7 hours in the elderly subjects. Significantly, the average peak concentrations relative to the average minimum concentrations during the sustained concentration time interval are only about 2:1 for the young and <3:1 for the elderly. These profiles and plasma concentrations are quite useful and unexpected for this dose in terms of amplitude and duration. The amplitude and duration are particularly surprising since these results are at least 10 times what were expected from 1% bioavailability.

FIG. 2 shows that 0.2 mg of melatonin with 20 µg of immediate release melatonin produces truly physiological plasma concentrations of melatonin, especially in the elderly. Because some elderly patients naturally produce some melatonin at night about one-third the melatonin of young subjects, the dose can be even further reduced in that segment of the population to about 0.15 mg or even 0.1 mg or less total melatonin, if desired to supplement normal production, in a manner that will allow plasma melatonin concentrations to mimic normal in terms of amplitude and duration.

These data show at least 5% bioavailability with a very low dose (less than 1 mg) from an oral sustained release melatonin composition with relatively non-variable results and sustained plasma melatonin concentrations that mimic a normal pattern. This type of product is useful to phase-shift circadian patterns or as a melatonin replacement or supplement in a patient who does not have a normal melatonin pattern. Administration may be at or near the patients normal sleep time, i.e., when the endogenous melatonin onset should begin; or administration may be several hours (4 or more) in advance of these times in order to mimic the normal melatonin pattern during the period of interest. Such administration will normally be of a very low melatonin dose yielding bioavailability of at least 10%. This level of bioavailability is adequate to produce a physiological profile of melatonin.

EXAMPLE 5

Production of Phase Advance by Melatonin Administration

1. Immediate release melatonin

The effect of exogenous melatonin administration on circadian rhythm of sighted people was tested. Eight normal subjects were treated in a two-week protocol, similar to the one used in Example 4. During the first week, the subjects were given a placebo at 1700 and 1900 hours and the time, extent and amount of dim light melatonin onset (DLMO) was measured as described in Example 2. During the second week, subjects were given placebo at 1700 and 1900 hours for two days, and then immediate release melatonin was administered orally in two doses of 0.25 mg at 1700 and 1900 hours for 4 days and the subject's DLMO determined.

Figure 3:
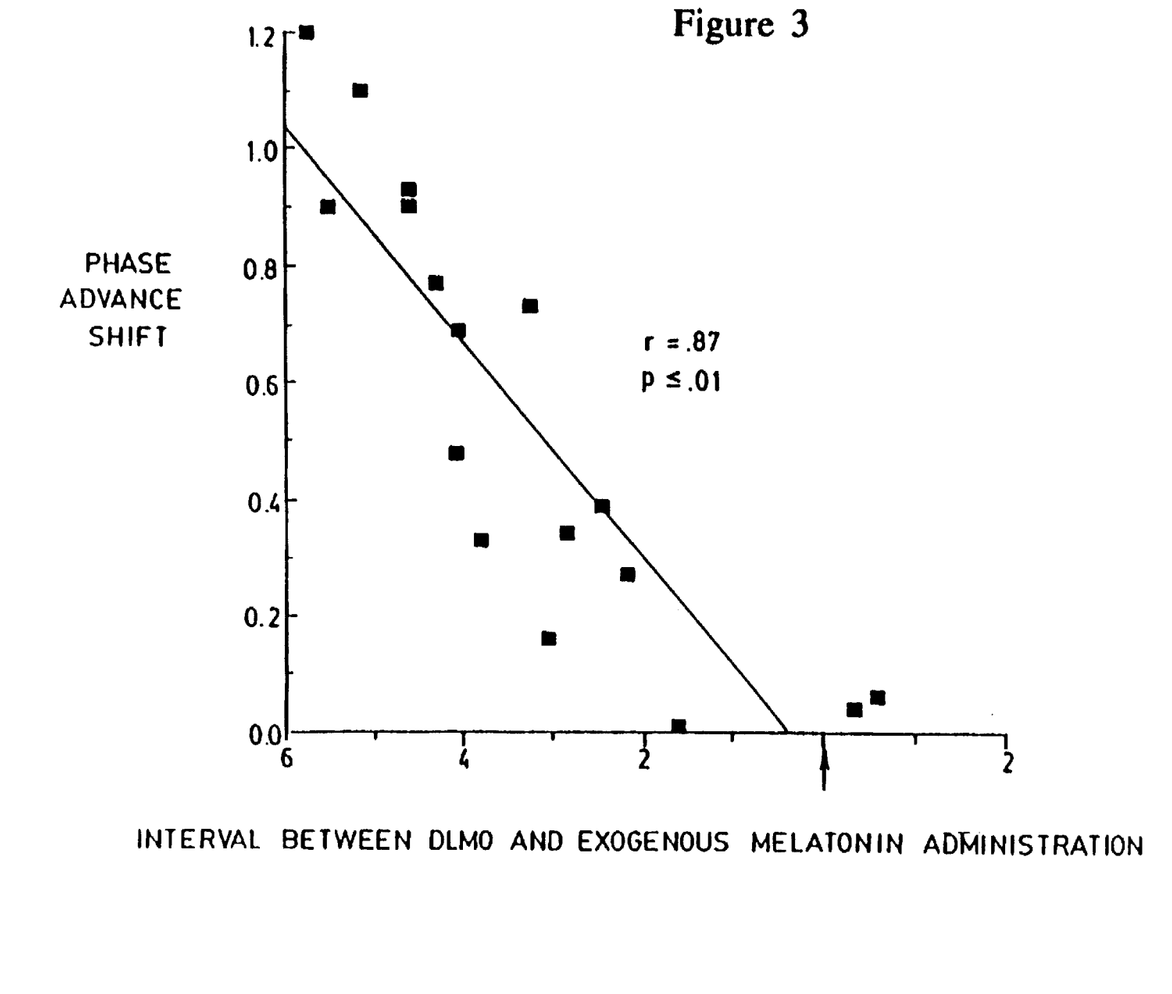
FIG. 3 discloses the experimental results of Example 5, and shows the relationship between the degree of phase shift obtained and the interval time of administration of exogenous melatonin and the endogenous dim light melatonin onset (DLMO).

Seventeen trials were conducted on the eight subjects. The results of this study are shown in FIG. 3. The Figure shows the relationship between the degree of phase shift obtained and the interval between the time of administration of exogenous melatonin and the endogenous DLMO. This interval is also known as the phase angle difference or phase angle. The earlier the exogenous melatonin is administered the greater is the magnitude of the phase advance; that is, there is a positive correlation between the extent of phase advance achieved by exogenous melatonin administration and the time interval between the time of exogenous melatonin administration and the time of endogenous melatonin onset. These results confirm that exogenous melatonin administration can effect a phase advance in humans, and that the timing of exogenous melatonin administration relative to the onset of endogenous melatonin is critically important for phase shifting the onset of the circadian rhythms.

2. Sustained Release Melatonin

Four sighted subjects, two female and two males, all ages 47–50, traveled from the west coast of the United States to Paris, France by jet leaving the original U.S. port of departure at about 7 AM (U.S. Pacific Time) and arriving in France at about 9 AM (France Time) the next day. Each subject was orally administered a melatonin capsule containing 0.27 mg of sustained release melatonin prepared essentially as described in part 1 of Example 1 at 1 PM (Pacific Time) on the departure day on the plane. The subjects rested and dozed during the flight. The subjects were administered a second dose of the same composition at about 10 PM to midnight bedtime in France (corresponding to about 1 to 3 PM Pacific time) on the arrival night and a third dose on the second night following the arrival at about 10 PM or midnight each night depending on the subject, that was about 1 PM or 3 PM Pacific Time. This was predicted to be about 6 hours before the normal DLMO.

All subjects had previously experienced jet lag when traveling over several time zones. It is known that their melatonin patterns would be out of phase with the local time and the DLMO phase delayed in France since the subjects were going to bed at times that were equal to the middle of the day at their departure city, and their melatonin production would be delayed and very low during the first hours in bed. Further, at 3 AM in France, it would be only 6 PM Pacific Time and it is common for travelers to awaken and have difficulty returning to sleep for several hours. All subjects experienced a tiredness and readily fell asleep following the low dose oral controlled release composition of melatonin and either slept through the night or, if they awakened, readily returned to sleep. Such low doses of melatonin with their very low input rates are not known to be soporific. Without wishing to be bound to any particular hypothesis, it is presently believed that the physiologic outcome for the subjects who traveled to and from France and took the oral sustained release melatonin is a result of circadian phase shiftings as well as mimicking a normal melatonin pattern, and that the same outcome could not be achieved without mimicking the normal pattern.

On the return to the U.S., the subjects took the same composition of oral controlled release melatonin for the first two nights following the return. In this case, the travelers left France at about 11 AM (France Time) and arrived on the west coast of the U.S. at about 9 PM Pacific time the same day. Each subject's circadian time was still on France time, however, as 9 PM Pacific time corresponded to 6 AM. Thus, a normal melatonin night pattern was not produced by the pineal gland. In this case, the melatonin was administered at about 11 PM Pacific Time, which is about 15 hours before the normal bedtime in France or about 13 hours before DLMO. Such schedules are known to disrupt sleep patterns and the effects are commonly referred to as "jet lag". However, the study subjects reported excellent sleep patterns following the melatonin administration and a substantial reduction in the symptoms associated with jet lag.

EXAMPLE 6

Phase-Shifting Effect of Exogenous Melatonin Administration

1. Phase advance

Figure 4:
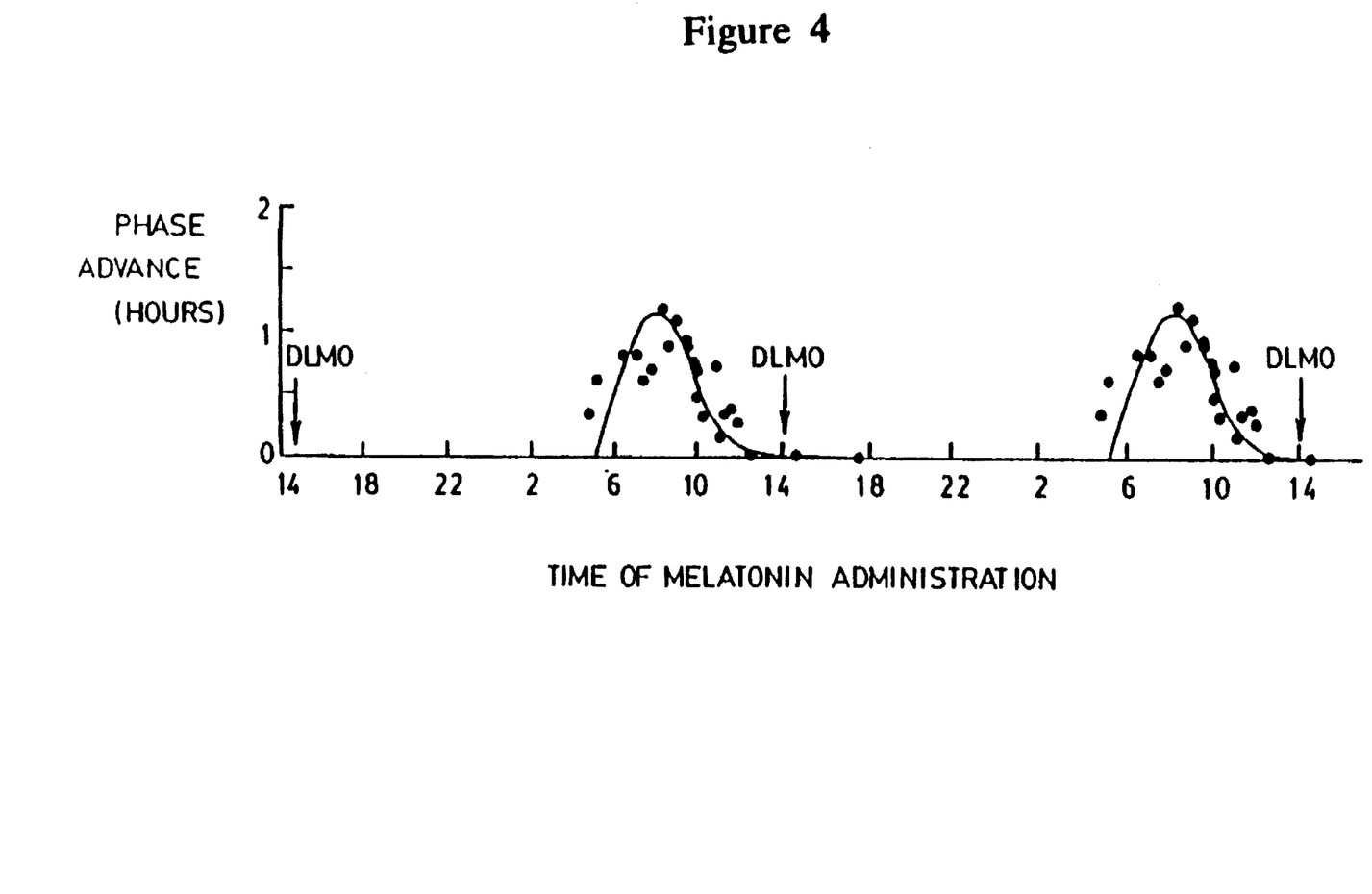
FIGS. 4 and 5 disclose the experimental results of part 1 of Example 6.
Figure 5:
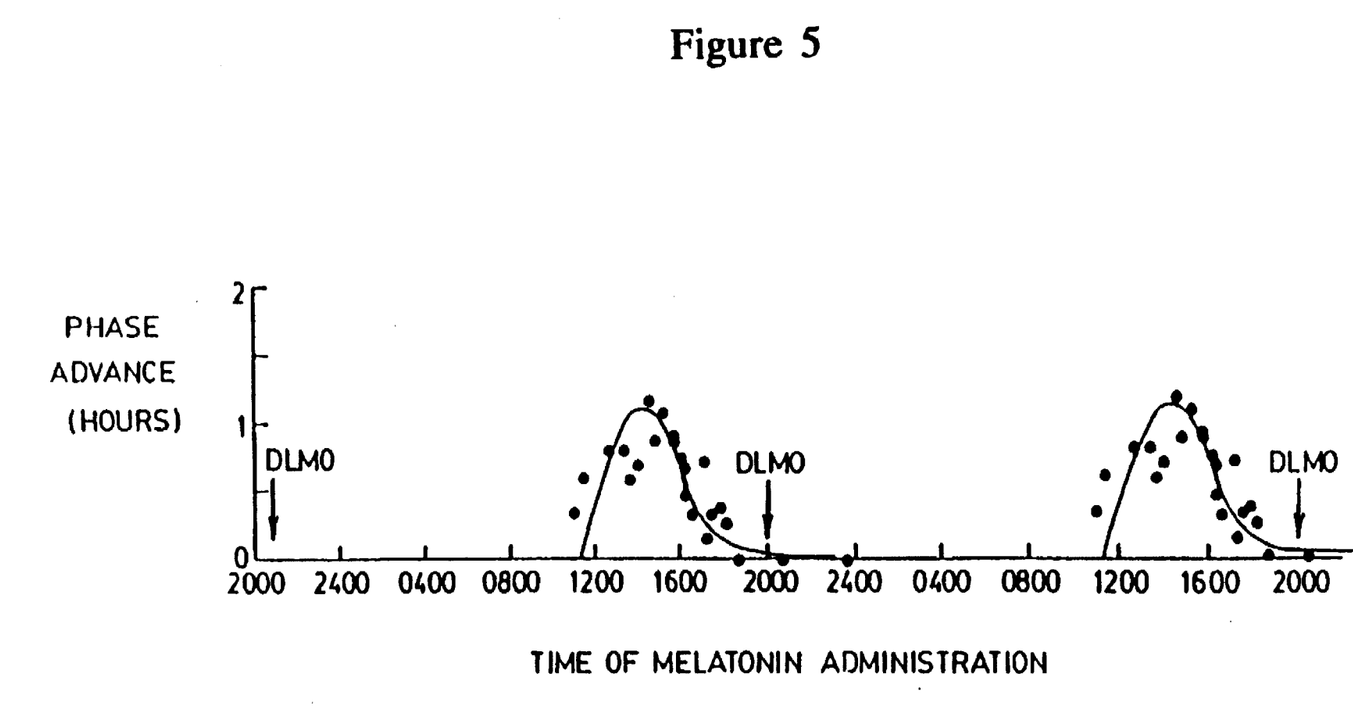

The effect of exogenous melatonin treatment administered at earlier times relative to the endogenous melatonin pattern was tested in sighted people. Twenty-four trials were conducted in the eight normal subjects who were treated in a two-week protocol similar to the one used in Example 5. During the first week, placebo was administered and the time of dim light melatonin onset (DLMO) was determined. Subsequently in the second week, melatonin was administered at various times prior to the time of endogenous melatonin onset, and the subject's endogenous melatonin onset was determined. The results of this study are shown in FIGS. 4 and 5. FIG. 4 expresses the results in terms of circadian time [assuming the DLMO occurs at circadian time (CT) 14], and FIG. 5 expresses the same results in terms of military time [assuming that DLMO is at 2000 hours (8 PM)]. These results show that the maximum degree of phase advance in the onset of endogenous melatonin occurred after administration of exogenous melatonin at circadian time (CT) 8, or 6 hours prior to the normal time of melatonin onset in the subjects (CT 14). This corresponds to a time of about 8–10 hours before normal bedtime in these subjects. The observed phase advance declines rapidly when exogenous melatonin is administered prior to CT 8. Between CT 8 and CT 14, the decline in the degree of advance is linear and proportional to the phase angle between time of administration and time of endogenous onset. Minimal effect, if any, on the circadian rhythm of endogenous melatonin onset is seen when the time of administration of exogenous melatonin coincides with the normal time of onset of endogenous melatonin (CT 14).

2. Phase delay

Experiments were conducted to investigate the use of exogenous melatonin to effect a phase delay. These experiments used essentially the same procedure as described above in part 1 of this Example except that the time of melatonin administration was altered.

Figure 6:
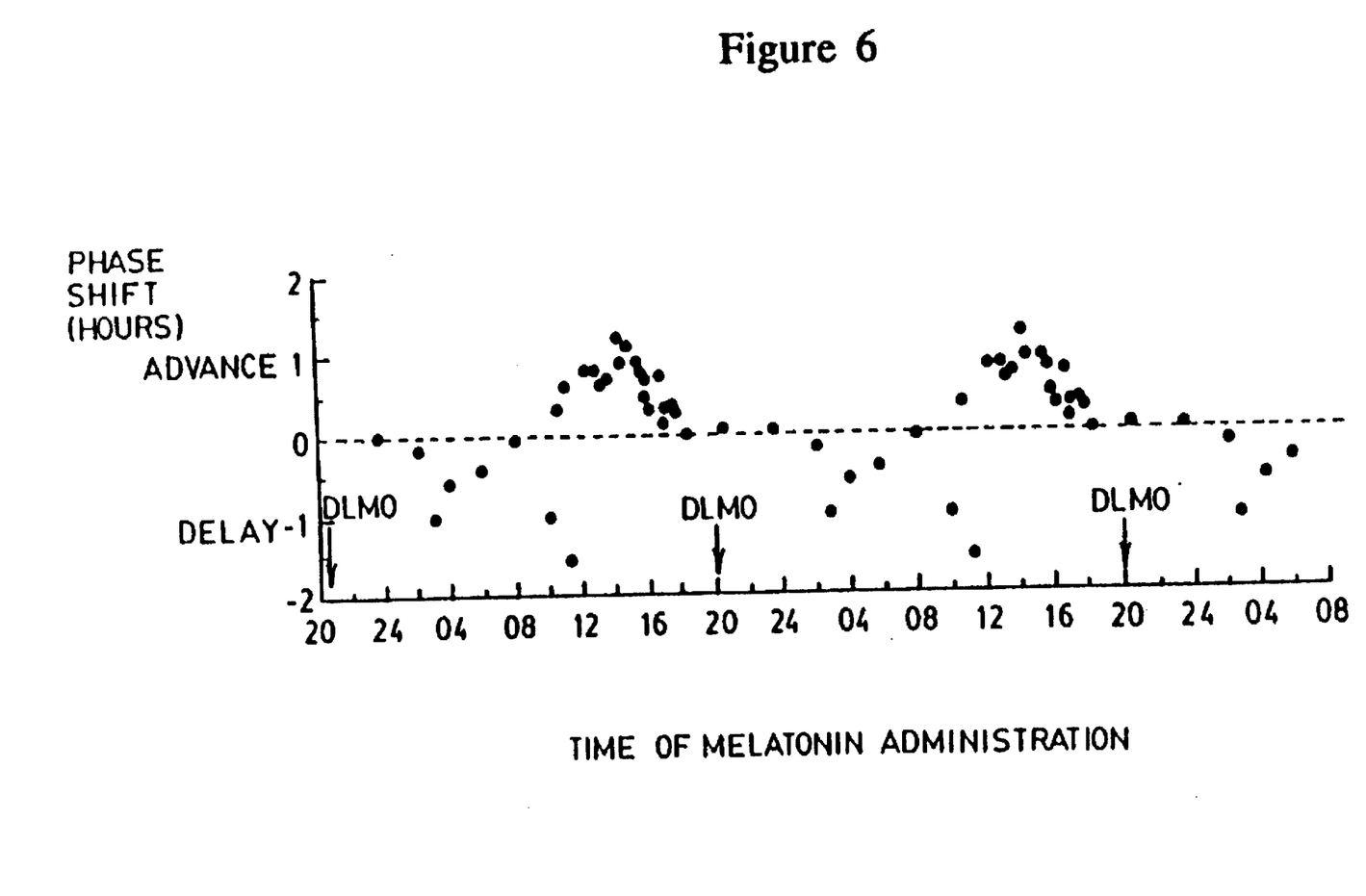
FIGS. 6 and 7 disclose the results of part 2 of Example 6 and are graphs of the time of melatonin administration versus phase shift in hours.
Figure 7:
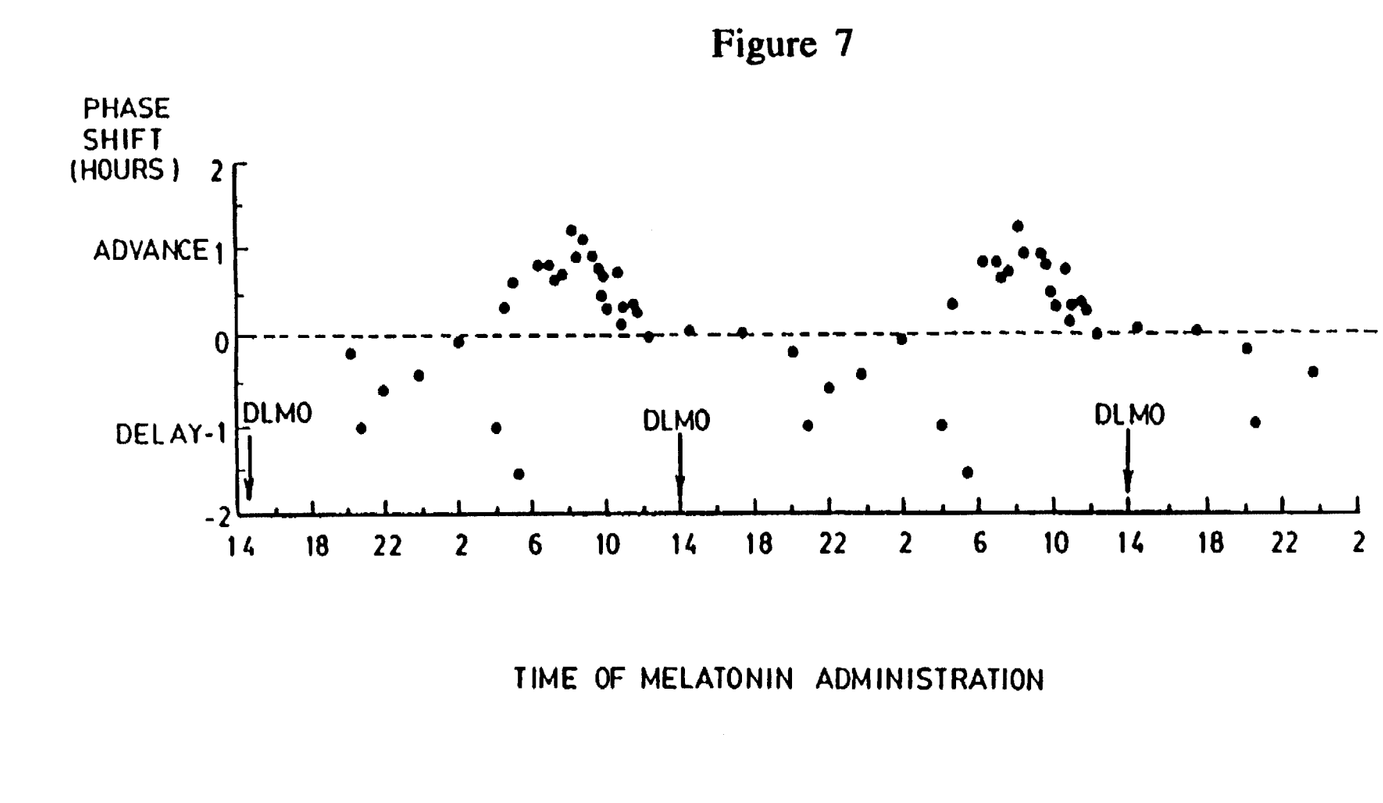

A total of 30 trials using 9 subjects were performed in which exogenous melatonin was administered about 11–19 hours before normal bedtime. Administration of exogenous melatonin from about 9–17 hours before the endogenous melatonin onset resulted in the greatest degree of phase delay in the onset of endogenous melatonin production. The results of these experiments are displayed as phase response curves (PRCs) and are shown in FIGS. 6 and 7.

The results of this example demonstrate that exogenous melatonin can be administered at a specific time relative to an individual's normal sleep phase or endogenous melatonin onset to achieve phase advance or a phase delay.

EXAMPLE 7

The Effect of Physiologic Melatonin Administration on Sleep in the Elderly

An 89-year-old woman in good health and taking no medications was determined to have low endogenous melatonin production as established by her overnight production of urinary 6-hydroxy melatonin, the major metabolite of melatonin. Her average overnight (1800 to 0900) production of 6-hydroxy melatonin was 967±248 (SD) ng. The average overnight production for females age 80 and above is 6000±S.D. 3,700 ngm, respectively, Sack et al., J. Pineal Res. 3: 379–388 (1986).

Sleep studies were carried out by a trained sleep technologist. An initial "diagnostic" PSG was performed on the first two nights to rule out significant primary sleep pathology. For the sleep study, a standard 16 channel montage was used: four EEG ($C_3A_2$, $O_1A_2$, $C_4A_1$, $O_2A_1$), four EMG (two for chin, one each for right and left lower extremity), one nasal air flow, two ocular movements, two for respiratory muscle movement, one for oximetry, one for body position and one for EKG. Subsequent recordings omitted the airflow and leg EMG channels. Sleep recordings were done in the subjects' own homes using portable Telediagnostics® polysomnograph, in order to minimize effects from the unfamiliar sleep laboratory environment. Sleep records were hand-scored using conventional criteria, as described by Rechtschaffen and Kales, Manual of Standardized Terminology: Techniques and Scoring System for Sleep Stages in Human Subjects, Los Angeles; UCLA Brain Information Service/Brain Research Institute, 1968. Technicians scoring sleep were blind to the treatment condition.

Two nights of in-home polysomnography were done at baseline and on the first two nights and last two nights of each treatment condition. Two treatment sequences were possible:

| (1) BASELINE | → | MELATONIN LDSR[1] 2 WEEKS | → | PLACEBO 2 WEEKS |
| (2) BASELINE | → | PLACEBO 2 WEEKS | → | MELATONIN LDSR 2 WEEKS |

[1]Low dose sustained release

The subject was assigned by chance to treatment sequence No. 2. Placebo was administered each night at bedtime for two weeks, followed by a two-week wash-out period, followed by two weeks of 0.2 mg slow-release melatonin capsules (prepared according to part 6 of Example 1) administered each night at bedtime. Ten PSG studies were done; two at baseline and two at both the start and end of each treatment sequence.

The diagnostic (baseline) sleep studied demonstrated a lack of sleep pathology. The data from the four nights of placebo treatment were averaged and compared to the average of the four nights of the active treatment. The results are shown in the following table. In summary, the average total recorded sleep period time (lights out to lights on) was about the same between the two conditions (difference=2.1 minutes), but total sleep time with melatonin treatment was increased 37.7 minutes. Also the wake after sleep onset was decreased by 35.7 minutes. Melatonin increased the time spent in Stage 2, 3 and 4 sleep, considered the deeper stages of sleep, and decreased the time spent in Stage 1 sleep, considered light sleep. Total non-REM and total slow wave sleep were increased. There was no apparent change in total REM sleep. There was no apparent change in sleep latency nor in REM latency. Both the number of movement arousals and transient arousals from sleep were decreased with melatonin treatment. Thus, melatonin treatment improved the quality of sleep.

TABLE 1

Sleep Study Statistice (Subject KA)
All data are averages for four nights[2]

|  | Sleep Period (SD) | Total Sleep (SD) | Wake After Sleep Onset (SD) |
|---|---|---|---|
| Melatonin | 477.3 ± 20.7 | 376.0 ± 12.4 | 101.4 ± 19.2 |
| Placebo | 475.1 ± 7.9 | 338.3 ± 12.8 | 137.0 ± 12.0 |
| Difference (Melatonin − placebo) | 2.1 | 37.7 | −36.7 |

|  | Total Stage 1 | Total Stage 2 | Total Stage 3 | Total Stage 4 | Total Non-REM | Total REM | Total Slow-Wave |
|---|---|---|---|---|---|---|---|
| Melatonin | 39.5 ± 20.1 | 243.6 ± 12.5 | 25.2 ± 5.1 | 5.8 ± 0.0 | 314.1 ± 15.2 | 62.0 ± 17.1 | 31.0 ± 5.1 |
| Placebo | 59.0 ± 16.2 | 206.6 ± 9.0 | 6.1 ± 1.8 | 0.0 ± 0.0 | 271.7 ± 12.4 | 66.6 ± 5.1 | 6.1 ± 1.8 |
| Difference (Melatonin − placebo) | −19.5 | 37.0 | 19.1 | 5.8 | 42.4 | −4.7 | 24.8 |

|  | Lights Out to S1 | Lights Out to S2 | Lights Out to REM | Movement Arousal during NREM | Transient Arousal during NREM |
|---|---|---|---|---|---|
| Melatonin | 17.8 | 23.8 | 67.7 | 21.4 | 58.2 |
|  | 19.8 | 19.3 | 50.8 | 28.7 | 85.0 |
| Placebo | 16.4 | 21.6 | 94.9 | 47.0 | 118.0 |
|  | 6.6 | 10.9 | 37.2 | 30.4 | 102.5 |
| Difference (Melatonin − placebo) | 1.4 | 21. | −7.2 | −25.6 | −59.8 |

[2]Units are in minutes.

EXAMPLE 8

Calculation of Bioavailable Melatonin from Serum Melatonin Concentrations

Input absorption rates and cumulative amounts of melatonin absorbed (bioavailability) were estimated using an interactive computer deconvolution program and pharmacokinetic parameters similar to those reported by Iguchi et al. In this case the program was PCDCON, version 1.0, created at the College of Pharmacy, University of Texas. Exact bioavailability was not determined in this study since an intravenous dose was not administered as a reference standard. This method estimates the bioavailability to be at least 5% from 0.2 mg, 0.4 mg and 0.8 mg formulations of the invention.

From the foregoing it will be appreciated that, although specific embodiments of the invention have been described herein for purposes of illustration, various modifications may be made without deviating from the spirit and scope of the invention.

What is claimed:

1. A dosage form comprising a sustained release melatonin formulation having a total dose of melatonin that is less than 1 mg, wherein a portion of the total dose of melatonin provided is in a sustained-release form and a portion of the total dose of melatonin provided is in an immediate release form, wherein the formulation provides at least 1% bioavailable melatonin and wherein the dosage form produces a plasma concentration profile for melatonin that mimics the normal nighttime melatonin plasma concentration profile when administered to a human.

2. The dosage form of claim 1 wherein the formulation releases melatonin over a period of about 3 to about 12 hours.

3. The dosage form of claim 1 wherein the formulation produces plasma melatonin concentrations in an animal that are from about 10 to about 600 pg/mL over a period of at least 3 hours.

4. The dosage form of claim 1 wherein the formulation produces a normal nighttime plasma melatonin concentration in an animal.

5. A dosage form of claim 1 wherein the sustained release melatonin formulation comprises:
  (a) a sugar-based core comprising less than 1 mg of melatonin where the melatonin is about 0.05 to 2% by weight of the core; and
  (b) about 5 to 25% by weight of ethylcellulose coating comprising ethylcellulose and a plasticizer.

6. The dosage form of claim 5 wherein the plasticizer is an alkyl sebacate or a trialkyl citrate, where each alkyl is the same or different and represents straight or branched chain alkyl groups having 1–6 carbon atoms.

7. The dosage form of claim 5 wherein the core additionally contains from about 0.05 to 1% by weight of polyvinylpyrrolidone and 0.01 to 1% by weight of hydroxypropylcellulose.

8. The dosage form of claim 5 wherein the core comprises about 0.3 % by weight of melatonin.

9. The dosage form of claim 1 that is orally administered.

10. A method for treating an animal suffering from a melatonin deficiency, the method comprising the step of administering to the animal an effective dose of the dosage form of claim 1.

11. The method of claim 10 wherein the animal is a human.

12. The method of claim 11 wherein the human is elderly.

13. The method of claim 11 wherein the human is an Alzheimer's disease patient.

14. The method according to claim 11 wherein the dosage form is administered to a human from about 4 to about 17 hours before a time characterized as the human's endogenous melatonin onset time.

15. The method according to claim 11 wherein the dosage form is administered to the human from about 6 to about 19 hours before a time characterized as the onset time of the human's normal or desired sleep phase.

16. The dosage form of claim 1 wherein the portion of the total dose of melatonin that is in a sustained-release form comprises from about 0.1 to about 0.9 mg melatonin.

17. The dosage form of claim 1 wherein the portion of the total dose of melatonin that is in an immediate release form comprises from about 0.01 to about 0.09 mg melatonin.

18. A method for inducing sleep in a human, the method comprising administering an amount of melatonin less than 1 mg to the human in an oral dosage form according to claim 1 designed to provide a sustained release of melatonin over time, wherein the dosage form is administered at a time that produces a plasma concentration profile for melatonin that mimics the normal nighttime plasma melatonin concentration profile during the human's sleep phase and produces sleep in the human.

19. The method of claim 18 wherein the human is elderly.

20. The method of claim 18 wherein the human is afflicted with a melatonin deficiency disorder.

21. The method of claim 18, wherein the human is an Alzheimer's disease patient.

* * * * *